United States Patent

Wegrzyn et al.

[11] Patent Number: 6,043,881
[45] Date of Patent: Mar. 28, 2000

[54] SAMPLE CELL FOR GASEOUS EMISSION SPECTROSCOPY

[76] Inventors: Joseph Wegrzyn, 2980 Carney Dr., Sanborn, N.Y. 14132; Mark Leonard Malczewski, 1186 Nash Rd. North, Tonawanda, N.Y. 14120

[21] Appl. No.: 09/035,792

[22] Filed: Mar. 6, 1998

[51] Int. Cl.$^7$ .................................................. G01J 3/30
[52] U.S. Cl. ...................... 356/316; 356/311; 356/417
[58] Field of Search ................................. 356/311, 316, 356/326, 417; G01J 3/30

[56] References Cited

U.S. PATENT DOCUMENTS

| | | | |
|---|---|---|---|
| 3,032,654 | 1/1962 | Fay et al. ................................. | 250/43.5 |
| 4,532,219 | 7/1985 | Hagen et al. ............................. | 436/155 |
| 4,719,403 | 1/1988 | Beischer ................................... | 323/234 |
| 4,784,677 | 11/1988 | Al-Chalabi ................................ | 62/37 |
| 4,801,209 | 1/1989 | Wadlow .................................... | 356/417 |
| 5,412,467 | 5/1995 | Malczewski et al. .................... | 356/316 |
| 5,831,728 | 11/1998 | Malczewski ............................. | 356/316 |

OTHER PUBLICATIONS

Malczewski et al., "Using emission spectroscopy to perform impurity analyses in UHP gases", *Canon Communications LLC*.

"Yanaco Trace Nitrogen Analyser", Model PEB–1000, *Yanagimoto Mfg. Co., Ltd.*

R.J. Walker, "Detector for trace amounts of nitrogen in helium", Nov. 4, 1985, *Cryogenics 1986*.

Ogino et al., "Development of a Detector for Ultratrace Nitrogen in Argon Using Low-Pressure, Capillary Glow Discharge Molecular Emission Spectrophotometry", *Anal. Chem.*, 1997, 69, 3636–3640.

*Primary Examiner*—Frank G. Font
*Assistant Examiner*—Layla G. Lauchman
*Attorney, Agent, or Firm*—Blake T. Biederman

[57] ABSTRACT

An electric discharge tube for a gas emission spectrometer and method for analyzing and measuring low concentration levels of multiple gas/vapor impurities in a gas stream under continuous flow conditions. The electric discharge tube comprises a plurality of analytical sites through which emissive radiation generated by an alternating source of power across the tube can be analyzed and measured.

13 Claims, 3 Drawing Sheets

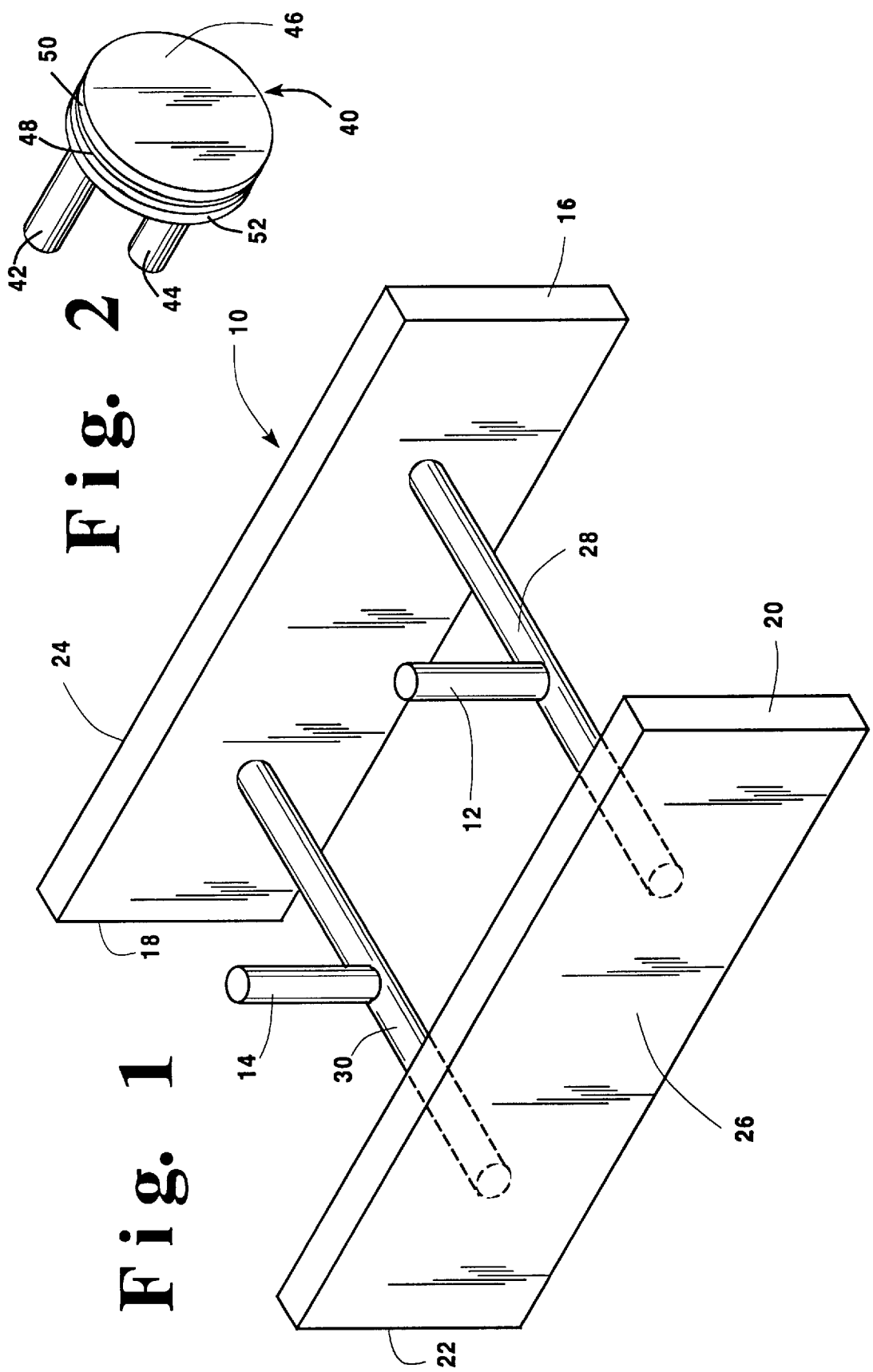

SAMPLE CELL FOR GASEOUS EMISSION SPECTROSCOPY

BACKGROUND OF THE INVENTION

The invention relates to gas emission spectrometers for analyzing a gas stream to detect and quantify the concentration of predetermined gaseous contaminants in a gas stream of mixed gases under continuous flow conditions. In particular, it relates to an improved electric discharge tube comprising one or more sample cells for a gas emission spectrometer, featuring a plurality of analytical sites, and a method for simultaneous analysis of a plurality of selected impurities.

An ultra high purity supply of inert gas, particularly argon, has become essential in the manufacture of large scale integrated circuits. Semiconductor manufacturers utilize commercial purifiers to remove impurities in the argon stream to less than 10 parts per billion (ppb). Some of the more important impurities removed by these purifiers include $O_2$, $H_2O$, CO, $H_2$, $CO_2$, $CH_4$ and $N_2$. Continuous monitoring of the inert gas stream under continuous flow conditions to assure that the gas stream purity continues to meet its stringent specifications is mandatory.

Currently the only method for continuous monitoring of nitrogen at low concentration levels in a high purity argon gas stream is emission spectroscopy. In emission spectroscopy the gases are excited in a gaseous discharge to produce optical emission lines characteristic of each gas in the gas stream. The emission line of nitrogen is then isolated and analyzed to measure its intensity in order to quantify its concentration.

The conventional emission spectrometer employs a dielectric pyrex tube having two electrodes extending therefrom to which an alternating electric field is applied at a high potential sufficient to cause an electric discharge. The gas sample is fed into the tube under continuous flow conditions and is excited by absorption of energy during the electric discharge. This results in the emission of radiant energy as the gas molecules drop from an elevated energy level to lower energy levels. The wavelengths of this emission are characteristic of the gas components excited by the absorption and release of energy. By filtering out unwanted wavelengths the intensity of the emission of any gas in the gas stream can be measured. In an argon gas stream, the concentration level of an impurity gas such as nitrogen can be measured by optically isolating light at the strongest characteristic wavelength for nitrogen i.e. at 337.1 nm and converting the separated optical signal to a corresponding electrical signal.

In conventional emission spectroscopy, the radiated output signal from the electric discharge source is modulated to produce an alternating signal using a mechanically rotating wheel sometimes colloquially referred to as a "chopper". The chopper, thus used to modulate the optical signal output from the electric discharge tube, produces a desired modulation frequency of e.g. 510 Hz. The modulated signal is then filtered to isolate the emission line 337.1 nm which is detected at the modulated frequency using signal electronics which includes a tuned amplifier to selectively amplify the 510 Hz modulated frequency signal and to reject other frequencies. A chopper has been used in emission spectroscopy for modulating the optical signal output of the silent electric discharge tube from its early inception. The function and need for a chopper in emission spectroscopy is described in detail in U.S. Pat. No. 3,032,654 issued May 1, 1962.

Another operation scheme for the operation of an emission spectrometer is described in detail in U.S. Pat. No. 5,412,467 issued May 2, 1995. In accordance with this disclosure, it was discovered that the use of a "chopper" and its function, which heretofore was deemed essential to the operation of an emission spectrometer, may be entirely eliminated. Instead the emissive radiation from the electrical discharge source was modulated by controlling the input frequency to the high voltage transformer and converted into a modulated electrical signal and amplified within a narrow frequency range centered at substantially twice the excitation frequency of the source of alternating voltage applied across the electric discharge source. This was reported to increase the sensitivity of detection of any gaseous impurity in the gas sample by an order of magnitude. In particular the range of detection of nitrogen in an argon gas sample using this concept was described as being extended to a level below 20 parts per billion (ppb).

The method pursuant to U.S. Pat. No. 5,412,467 for analyzing a continuously flowing gas stream at concentration levels extending below 20 parts per billion using emission spectroscopy comprises the steps of:

directing a sample of the gas stream through an electric discharge source;

applying an alternating source of power across said electric discharge source at a preselected excitation frequency with said alternating power source having a peak voltage sufficient to sustain an electric discharge and to generate a wide radiation spectrum of emissive radiation from said gas stream;

filtering said radiation spectrum to form an optical signal having a narrow radiation emission bandwidth corresponding to the stronger emission wavelength(s) of a preselected gas or vapor impurity to be analyzed;

converting said optical signal into an electrical signal;

selectively amplifying said electrical signal within a narrow frequency range centered at substantially twice said excitation frequency; and analyzing said selectively amplified electrical signal to determine the concentration level of the gas or vapor under analysis.

Utilizing this method, an improved gas emission spectrometer was disclosed comprising: a silent electric discharge source; means for feeding a gas sample through said discharge source at a preselected flow rate; power supply means for applying a source of alternating voltage across said silent discharge tube at a predetermined excitation frequency and of sufficient peak voltage predetermined excitation frequency and having sufficient peak voltage to sustain an electric discharge and generate emissive radiation from said gas stream over a wide radiation spectrum; means for optically filtering said radiation spectrum to form an optical signal having a narrow radiation emission bandwidth corresponding to the stronger emission wavelength(s) of a preselected gas impurity for detection in said gas sample; means for converting said optical signal into a corresponding electrical signal and analog amplifier means for selectively amplifying said electrical signal within a narrow frequency range centered at substantially twice the excitation frequency whereby the sensitivity of detection of said gas impurity is increased to a minimum detection level (MDL) of below 20 parts per billion (ppb).

Previous gaseous emission spectrometers, such as that described in U.S. Pat. No. 3,032,654, were designed to analyze a single impurity such as nitrogen in a sample gas such as argon. Accordingly, only a single analytical tube and a single photomultiplier detector was required. This analytical tube typically was rugged and relatively easy to assemble, as it consisted of thick plate glass and spacers epoxied together. The thickness of the plate glass and the spacers resulted in a relatively wide electrode gap of 9/16 inch. The electrode gap, however, is a key parameter in determining the voltage necessary to initiate the plasma discharge in the sample gas stream. At a gap of 9/16 inch, approximately 7000 VAC is necessary to sustain the plasma even in an easily excitable sample gas such as argon. In order to supply such a voltage continuously for long periods of time, a large, bulky transformer is required. In addition, in constructing such an analytical tube using conventional techniques, epoxy typically was used to seal joints and seams; with epoxy, off-gassing and risk of air leakage into the cell can degrade the sample gas purity.

Accordingly, there is a need to develop an improved analytical tube and method of analysis to detect multiple selected impurities in a gas stream of mixed gases under continuous flow conditions, particularly employing a configuration wherein the capability of multiple analysis does not result in the need for duplicative analysis equipment and the attendant increase in overall unit bulk and size.

SUMMARY OF THE INVENTION

Now, an improved gas emission spectroscopy method for analysis of a plurality of selected gas impurities in a gas stream has been developed. In addition, an improved electric discharge tube for a gas emission spectrophotometer has been developed, whereby simultaneous analysis of a plurality of gas or vapor impurities can be accomplished.

The preferred electric discharge tube is a "silent electric discharge tube" based on the principles taught by H. Fay in U.S. Pat. No. 2,943,223, the disclosure of which is incorporated hereby by reference. In general, a typical electric discharge analyzer tube is composed of a pyrex glass tube which has been flattened on a mandrel to form a rectangular geometry with flat sides to which electrodes are attached. The electrodes are connected to an input power supply including a high voltage ionization transfer and a variable frequency oscillator. As is further described by Malczewski et al. in U.S. Pat. No. 5,412,467, the disclosure of which is incorporated hereby reference, line voltage from a conventional AC line supply of E.G. 120 volt 60 Hz is connected to the variable frequency oscillator of the input power supply. The variable frequency oscillator may be of any conventional design which permits adjustment of the frequency of the output of the power supply (hereinafter referred to as the "excitation frequency") applied to the electric discharge tube. The excitation frequency may be adjusted from a ratio of one to one relative to the AC line supply frequency to any desired multiple or fraction thereof. The high voltage ionization transfer is also conventional in design and steps up the output voltage of the input power supply to the required voltage necessary to sustain an electric discharge between the electrodes in the electric discharge analyzer tube. The required voltage necessary to sustain an electric discharge is typically of the order of many thousands of volts. Accordingly, the ionization transformer must be able to multiply the line voltage by a large multiple of e.g. 60 for a line voltage of 120 volts to provide a typical input voltage of 7200 volts.

The analyzer tube has an input port and an output port for passing a sample of gas through the analyzer tube at a controlled flow rate. An adjustable valve may be used to adjust the pressure and rate of flow of the sample gas from the gas supply manifold into the analyzer tube to within a more desirable flow range of typically between 1–4 SCFH at atmospheric pressure. Any gas composition may be analyzed in the analyzer tube under continuous flow conditions by the method of the present invention provided it has an optical emission characteristic which permits detection by emission spectroscopy.

An optical filter is used to isolate the emission line of the gas impurity to be analyzed. The optical filter must therefore have a very narrow bandpass to eliminate the broad spectrum of light emitted form the silent electric discharge source. For example, to detect nitrogen in a gas sample of argon the emission line of interest is 337.1 nm.

A photomultiplier of conventional design is used to convert the isolated optical signal transmitted from the optical filter to a corresponding electrical output signal. The photomultiplier should have a maximum spectral response near the emission line of interest for the impurity gas to be detected.

The electrical output signal from the photomultiplier may be fed to any conventional analog amplifier capable of selectively amplifying the signal within a narrow range of frequencies centered, in accordance with the present invention, at approximately twice the excitation frequency of the input power supply. The analog amplifier may represent a conventional "lock-in" amplifier as is known to those skilled in the art which amplifies the signal at a frequency corresponding to an adjustable reference frequency signal to be set at twice the excitation frequency or may be represented by a "tuned amplifier" which acts to select a very narrow frequency band out of the electrical signal which for the present invention would be equal to approximately twice the excitation frequency of the input power supply. A conventional "tuned amplifier" design includes one or more operational amplifiers, with its maximum response centered or "tuned" to equal twice the excitation frequency of the input power supply. Accordingly, the analog amplifier will amplify signals only at approximately twice the excitation frequency of the input power supply. Separate DC power supplies provide power for the photomultiplier and the analog amplifier respectively.

The output signal from the analog amplifier is rectified into a DC signal which provides an indication of the magnitude of the level of gas impurity for display on a monitor and/or for driving a recorder which may be calibrated for the analysis of a specific impurity measurement.

The optical signal from the discharge tube is filtered and converted to an electrical signal which is amplified by an analog amplifier for selective amplification of the electrical signal at essentially twice the excitation frequency of the input power supply. Although any excitation frequency may be used it is preferred to operate with a power supply excitation frequency of 255 Hz or greater. This results in an increase in sensitivity in detecting the presence of an impurity in the gas sample.

By changing the wavelength selected by the optical filter, the spectrometer of the present invention may be made to analyze for any impurity that has a suitable emission line in the UV or visible spectrum. As an example, changing the optical wavelength from 337.1 nm to 308.0 nm would enable moisture to be analyzed whereas by changing the wavelength to 430.0 nm would permit methane to be analyzed. Moreover, the analysis can be performed using a gas stream of base gases other than argon. The operating pressure and the geometry of the discharge tube favor the excitation of the component of gas mixture with the lower ionization potential. Nitrogen can be analyzed in argon because of the lower ionization potential of nitrogen relative to argon. Therefore, any base gas can be used which has a higher ionization potential than the impurity gas or vapor. Accordingly, for example, impurities selected from a group consisting of nitrogen, carbon monoxide, carbon dioxide, oxygen, methane, hydrogen, and water may readily be analyzed for their presence as an impurity in base gases other than argon such as, for example, helium (He), neon (Ne), and Krypton (Kr) respectively or mixtures thereof.

In the standard arrangement as described in U.S. Pat. No. 5,412,467, radiation emission is analyzed from one specific end (analytical site) of the silent discharge tube to measure the concentration of a specific gas impurity. The complimentary opposite end of the discharge tube also can be used at the same time as an analytical site for analyzing the radiation emission spectrum for the presence of a second gas impurity independent of the analysis of the radiation emission from the first analytical site of the discharge tube. A second optical filter is used having a wavelength corresponding to the second gas impurity of, for example, 308 nm if the second gas impurity is moisture while the first optical filter is selected to analyze for nitrogen or methane. A second photomultiplier tube and analog amplifier is used to duplicate the function of the first photomultiplier and analog amplifier to analyze and measure the concentration of the second gas impurity simultaneous with the analysis of the first gas impurity. The analysis operation for each gas is independent of one another and is non-interfering. This arrangement is distinct from using, for example, a beam splitter to analyze for two gas impurities from the same emitted radiation. The geometry of the typical electric discharge analyzer tube, however, limits the capability of simultaneous analysis to two impurities, one at each analytical site at the ends of the discharge tube.

Now, an improved method for analyzing a continuously flowing gas stream using gas emission spectroscopy has been developed, whereby the presence of three or more gas or vapor impurities in the gas stream can be detected at low concentration levels. According to the present invented method, a sample of the gas stream is directed through an electric discharge analytical tube including one or more sample cells, said analytical tube having three or more analytical sites through which emissive radiation from the gas stream is generated, said one or more sample cells set within an electric discharge source, applying an alternating source of power across said electric discharge source to generate a wide spectrum of emissive radiation from said gas stream; and analyzing the emissive radiation simultaneously at the plurality of analytical sites to determine the concentrations of the gases or vapors under analysis.

The present invention also relates to an improved electric discharge analytical tube for use in a gas emission spectrometer for analyzing and measuring low concentrations of a plurality of gas/vapor impurities in a gas stream under continuous flow conditions. The electric discharge analytical tube comprises one or more sample cells and has three or more analytical sites through which emissive radiation generated by an alternating source of power across said one or more sample cells can be analyzed and measured.

BRIEF DESCRIPTION OF THE DRAWINGS

For further understanding of the present invention, reference should be made to the following detailed description of a preferred embodiment taken in conjunction with the accompanying drawings in which like elements have been given like reference numerals, and wherein:

FIG. 1 shows a perspective view of an electric discharge analytical tube wherein a sample gas is diverted into two parallel sample cells with four analytical sites, one at each of the respective ends thereof.

FIG. 2 shows a perspective view of another embodiment of an electric discharge analytical tube wherein the single sample cell is circular in shape with a plurality of a analytical sites provided around its circumferential edge.

DETAILED DESCRIPTION OF PREFERRED EMBODIMENTS

Figure 3:
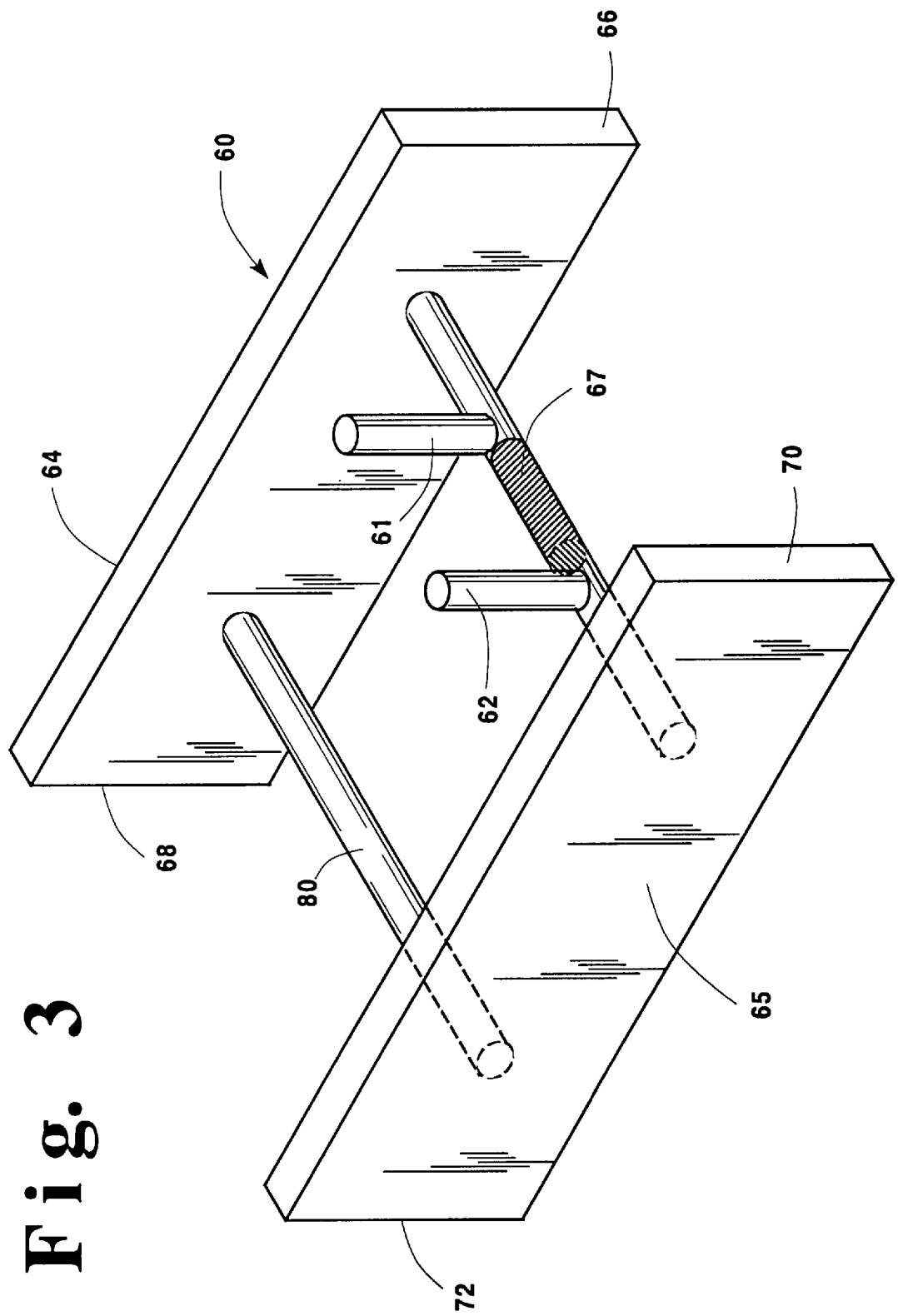
FIG. 3 shows a perspective view of an electric discharge analytical tube wherein a sample gas is directed serially through two sample cells with four analytical sites, one at each of the respective ends thereof.

A preferred embodiment of an electric discharge analyzer tube is shown in FIG. 1. The analyzer tube 10 has an input port 12 and an output port 14 for passing a sample of gas through the analyzer tube 10 at a controlled flow rate. A gas supply manifold fitted with an adjustable valve (not shown) may be used to adjust the pressure and rate of flow of the sample gas into the analyzer tube to meet desirable flow ratio and pressure. Any gas composition may be analyzed in the analyzer tube under continuous flow conditions provided it has an optical emission characteristic which permits detection by emission spectroscopy.

In operation, gas flows into the analyzer tube through port 12 and is diverted into two paths at conduit 28. The split flow proceeds through parallel cells 24 and 26 and exits conduit 30 and output port 14. A power supply applies the voltage necessary to sustain an electric discharge between electrodes (not shown) mounted on opposite sides of the respective sample cells. Radiation emission from the gas sample is analyzed through each of the plurality of analytical sites 16, 18, 20 and 22 at the ends of the parallel cells. A different optical filter is employed at each analytical site to isolate the emission line of the gas impurity to be analyzed. Accordingly, the presence of each of four gas impurities can be simultaneously analyzed independent of the analysis of the radiation emission of the others. Photomultiplier tubes and analog amplifiers can be mounted at each of the analytical sites to achieve simultaneous, independent, non-interfering analysis.

A particularly preferred embodiment of the invention is depicted in FIG. 2 wherein an analyzer tube 40 has an input tube 42 and an output tube 44 for passing a gas sample through a circular sample cell 46 having back plate 50 and front plate 52. Sample cell 46 offers the advantage of having a plurality of analytical sites all along its circumferential edge 48, around which a plurality of photomultiplier tube detectors can be arranged. Also, this embodiment readily can be fabricated all in quartz, completely fused, without the need for epoxy seals. This arrangement greatly enhances the integrity of the analyzer tube, and further accommodates the analysis of corrosive specialty gases which otherwise would attack epoxy seals.

Another embodiment of the invention is illustrated in FIG. 3. The analyzer tube 60 has an input port 61 and an output port 62, seperated by obstruction 67, for passing a sample of gas through the analyzer tube 60 at a controlled flow rate. A gas supply manifold fitted with an adjustable valve (not shown) may be used to adjust the pressure and rate of flow of the sample gas into the analyzer tube to meet desirable flow ratio and pressure. Any gas composition may be analyzed in the analyzer tube under continuous flow conditions provided it has an optical emission characteristic which permits detection by emission spectroscopy.

In operation, gas flows into the analyzer tube through port 61 and proceeds sequentially through serial cell 64, conduit 80 and serial cell 65. A power supply applies the voltage necessary to sustain an electric discharge between electrodes (not shown) mounted on opposite sides of the respective sample cells. Radiation emission from the gas sample is analyzed through each of the plurality of analytical sites 66, 68, 70 and 72 at the ends of the respective cells. A different optical-filter is employed at each analytical site to isolate the emission line of the gas impurity to be analyzed. Accordingly, the presence of each of four gas impurities can be simultaneously analyzed independent of the analysis of the radiation emission of the others. Photomultiplier tubes and analog amplifiers can be mounted at each of the analytical sites to achieve simultaneous, independent, non-interfering analysis.

Figure 4:
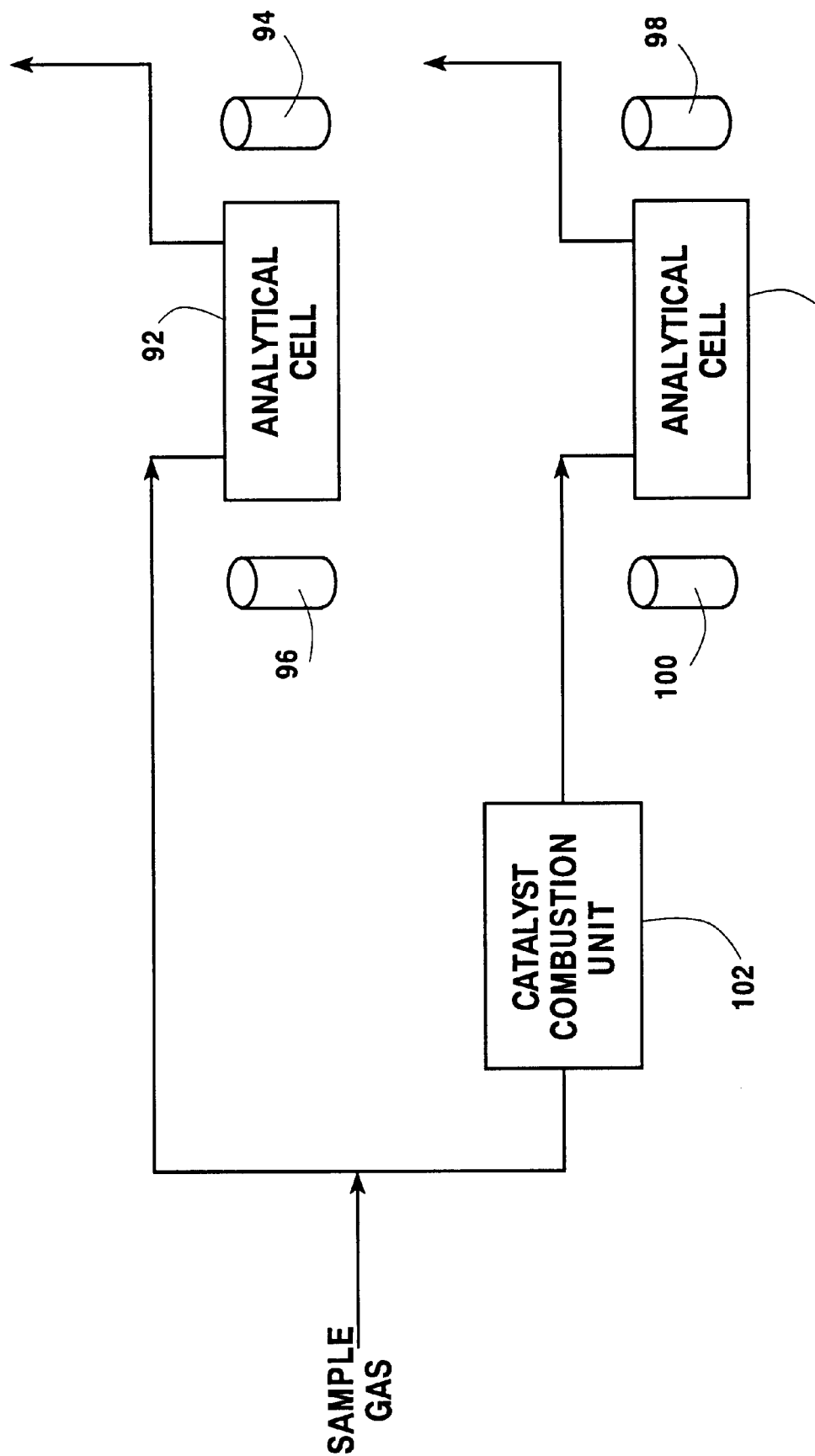
FIG. 4 is a schematic block diagram of an analytical cell arrangement in an emission spectrometer, wherein a sample gas is routed through two independent electric discharge analytical tubes to accomplish simultaneous analysis of impurities in a gas stream where one analyzed impurity must be converted to another analyzed impurity in order to be detected and measured by calculation of differences.

In FIG. 4, an arrangement is depicted a gas sample is routed to two independent analytical cells 90 and 92. Photomultiplier tube detectors 94, 96, 98, and 100 are positioned at each of the analytical sites at the ends of the analytical cells achieve simultaneous, independent, non-interfering analysis. Rather than routing the same sample sequentially through each analytical cell, independent gas samples are directed to each analytical cell 90 and 92. This arrangement offers an advantage if, for example, an impurity to be analyzed has to be converted to another impurity to be analyzed in order to be detected and measured. To illustrate, hydrogen might be an impurity desired to be analyzed, but it cannot be measured directly by this analytical technique. However, it can be measured if the hydrogen content first is converted to water. This conversion can be accomplished through the use of a conventional conversion catalyst. But, this approach is complicated if moisture also is present as an impurity in the gas stream, and this conversion technique only results in an analysis which represents the sum of the hydrogen and moisture contents.

Previous techniques alternately switches a sample gas stream first through and then around a conversion catalyst; first the hydrogen converted to water and the pre-existing moisture is measured, and then only the moisture is measured when bypassing the converter catalyst. Hydrogen content in the gas sample then is determined by difference. Using this previous method, however, does not provide simultaneous measurement, so that the determination of hydrogen content by difference is not strictly accurate and correct. In addition, for the period of time that the catalyst converter is being bypassed, there is no sample flow through the catalyst, which tends to degrade the response time of the analyzer.

Using the arrangement of the present invention, a sample gas stream is passed directly into first analytical cell 92, where, for example water and nitrogen are analyzed and measured by photomultiplier detectors 94 and 96, at the respective analytical sites at the ends of the analytical cell 92. A separate stream of sample gas passes through catalyst combustion unit 102, which combines the hydrogen content of the gas with oxygen to convert it to water, and then the gas stream passes through analytical cell 90, where total water is detected and measured by one photomultiplier detector 98, while the other photomultiplier detector 100 analyzes other impurities. Actual hydrogen content of the gas stream then can accurately be calculated by differences.

Various other modifications of the disclosed embodiments, as well as other embodiments of the invention, will be apparent to those skilled in the art upon reference to this description, or may be made without departing from the spirit and scope of the invention defined in the appended claims.

We claim:

1. A method for analyzing a continuously flowing gas stream using gas emission spectroscopy to detect a presence of a plurality of gas or vapor impurities in the gas stream at low concentration levels comprising:

directing a sample of the gas stream through one or more electric discharge analytical tubes having two or more sample cells through which the gas stream is directed in either parallel or serial flow paths and a plurality of analytical sites;

applying an alternating source of power across an electric discharge source, within which the electric discharge analytical tube is set, to generate a wide spectrum of emissive radiation from said gas stream;

analyzing the emissive radiation simultaneously at each of the plurality of analytical sites to determine the concentration of the plurality of gases or vapors under analysis.

2. The method of claim 1 wherein the gas stream is directed in parallel flow paths.

3. The method of claim 1 wherein said sample cells consist of two electric discharge analytical tubes and the gas stream is directed in parallel flow paths.

4. The method of claim 3 wherein the sample of gas stream is passed through a conversion analyst to convert one gas or vapor under analysis to another gas or vapor under analysis before said sample passes through one of the sample cells.

5. The method of claim 1 wherein the gas stream is directed in a serial flow path.

6. The method of claim 1 wherein said gas stream comprises a base gas selected from the group consisting of argon, helium, krypton, and mixtures thereof.

7. The method of claim 6 wherein said gas stream impurities are selected from a group consisting of nitrogen, carbon monoxide, carbon dioxide, oxygen, methane, hydrogen, and water.

8. The method of claim 1 wherein said gas stream impurities are analyzed and measured through analytical sites at opposite ends of the sample cells.

9. An electric discharge tube for a gas emission spectrometer for analyzing and measuring low concentrations of a plurality of gas stream impurities, comprising two or more sample cells through which a gas stream can be directed either in parallel or serial flow paths, and a plurality of analytical sites through which emissive radiation generated by an alternating source of power across said analytical discharge tube can be analyzed and measured.

10. The electric discharge tube of claim 9 wherein the two or more sample cells are connected in parallel.

11. The electric discharge tube of claim 9 wherein the two or more sample cells are connected in serial.

12. The electric discharge tube of claim 9 wherein the sample cells have analytical sites at the opposite ends of each of said cells.

13. An electric discharge tube for a gas emission spectrometer for analyzing and measuring low concentrations of a plurality of gas stream impurities, comprising a circular sample cell having a circumference and a plurality of analytical sites around the circumference through which emissive radiation generated by an alternating source of power across said analytical discharge tube can be analyzed and measured.

\* \* \* \* \*

UNITED STATES PATENT AND TRADEMARK OFFICE
CERTIFICATE OF CORRECTION

PATENT NO. : 6,043,881
DATED : March 28, 2000
INVENTOR(S) : Wegrzyn et al.

It is certified that error appears in the above-identified patent and that said Letters Patent is hereby corrected as shown below:

<u>Title page,</u>
After Item [76], Inventors, insert:
-- [73] Assignee: Praxair Technology, Inc., Danbury, Conn. --

Signed and Sealed this

Twentieth Day of August, 2002

Attest:

Attesting Officer

JAMES E. ROGAN
*Director of the United States Patent and Trademark Office*